United States Patent [19]
Chee

[11] Patent Number: 6,017,323
[45] Date of Patent: *Jan. 25, 2000

[54] BALLOON CATHETER WITH DISTAL INFUSION SECTION

[75] Inventor: Uriel Hiram Chee, San Carlos, Calif.

[73] Assignee: Target Therapeutics, Inc., Fremont, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/835,535

[22] Filed: Apr. 8, 1997

[51] Int. Cl.$^7$ .................................................. A61M 29/00
[52] U.S. Cl. ............................ 604/96; 604/527; 604/249
[58] Field of Search ............................ 604/96, 102, 246, 604/249, 524, 526, 527; 606/192, 194

[56] References Cited

U.S. PATENT DOCUMENTS

| | | |
|---|---|---|
| Re. 34,633 | 6/1994 | Sos et al. . |
| 3,174,851 | 3/1965 | Buehler et al. . |
| 3,351,463 | 11/1967 | Rozner et al. . |
| 3,753,700 | 8/1973 | Harrison et al. . |
| 4,646,742 | 3/1987 | Packard et al. . |
| 4,813,934 | 3/1989 | Engelson et al. . |
| 4,848,344 | 7/1989 | Sos et al. . |
| 5,035,705 | 7/1991 | Burns . |
| 5,135,494 | 8/1992 | Engelson et al. . |
| 5,171,221 | 12/1992 | Samson . |
| 5,207,229 | 5/1993 | Winters . |
| 5,250,034 | 10/1993 | Appling et al. . |
| 5,267,979 | 12/1993 | Appling et al. . |
| 5,304,198 | 4/1994 | Samson . |
| 5,318,535 | 6/1994 | Miraki . |
| 5,320,604 | 6/1994 | Walker et al. . |
| 5,380,282 | 1/1995 | Burns . |
| 5,380,307 | 1/1995 | Chee et al. . |
| 5,437,632 | 8/1995 | Engelson . |
| 5,454,788 | 10/1995 | Walker et al. . |
| 5,484,409 | 1/1996 | Atkinson et al. . |

FOREIGN PATENT DOCUMENTS 9-70438  3/1997  Japan .

OTHER PUBLICATIONS

WPAT Database English Abstract of EP 750919 which corresponds to JP Priority Patent Publication No. 9–70438.

*Primary Examiner*—Corrine McDermott
*Attorney, Agent, or Firm*—Morrson & Foerster LLP

[57] ABSTRACT

This is a single lumen balloon catheter having an infusion section distal of that balloon for infusing liquids into the bloodstream. In general, the infusion section has a plurality of holes in the wall of the section proximal of the tip so to allow infusion of that selected material. Depending upon the variation of the invention selected, the infusion section may have valve seats at either or both ends of that infusion section. The device may include a core wire for assistance in controlling the infusion of liquids through the distal sections orifices. The core wire, in most variations of the invention, may also be used as a guidewire for introducing the catheter with its attendant balloon to a suitable site. The single lumen is used both for inflation of the balloon and infusion of the treatment or diagnostic material. The balloon itself, depending upon the use to which the catheter is to be placed, may be either a compliant balloon or one having a predetermined fixed diameter.

39 Claims, 9 Drawing Sheets

BALLOON CATHETER WITH DISTAL INFUSION SECTION

FIELD OF THE INVENTION

This invention is a surgical device. In particular it is a single lumen balloon catheter having a section distal of balloon for infusing liquids into the bloodstream. In general, the infusion section has a plurality of holes in the wall of the section proximal of the tip so to allow infusion of that selected material. Depending upon the variation of the invention selected, the infusion section may have a valve seat at either or both ends of that infusion section. The device may include a core wire for assistance in controlling the infusion of liquids through the distal sections orifices. The core wire, in most variations of the invention, may also be used as a guidewire for introducing the catheter with its attendant balloon to a suitable site. The single lumen is used both for inflation of the balloon and infusion of the treatment or diagnostic material. The balloon itself, depending upon the use to which the catheter is to be placed, may be either a compliant balloon or one having a predetermined fixed diameter.

BACKGROUND OF THE INVENTION

This invention relates generally to a balloon catheter having an infusion section distal of the balloon. It is a single lumen catheter. The form of the catheter is such that it may used variously in procedures such as percutaneous transluminal angioplasty (PTA) procedures but is sufficiently flexible in its construction that it may be used for other diagnostic and treatment indications. This balloon catheter is especially useful for isolating a region of the vasculature to be treated and providing a measure of fluid to a limited region distal of the balloon. Because of the presence of only a single balloon region, it is significantly more flexible than other multiple balloon designs and is more readily controlled.

For instance, in percutaneous transluminal catheter angioplasty (PTCA) procedures, a guiding catheter often with a preshaped tip is introduced into the vasculature of a patient. The catheter is initially placed into the human body at a convenient site such as the femoral artery in the groin. The catheter is then advanced throughout the trunk of the body and up into the aortic arch near the heart. Once in that region, the catheter is twisted or torqued from the proximal end so that the preshaped distal tip of the guiding catheter has engaged the ostium of a desired coronary artery. A balloon-bearing catheter is then advanced through the guided catheter, out its distal tip until the balloon on the distal extremity of the dilatation catheter extends across the region to be dilated, and the balloon is then expanded. Expansion of the balloon is typically to a predetermined size and is dictated by the design of the balloon. Often a radio-opaque fluid is used to inflate the balloon a relatively high pressure so to permit the inflation to be observed. Upon completion of the procedure, the balloon is then deflated so that the dilation catheter may be removed and blood flow resume from the thus treated artery. In some instances it may desirable to introduce some amount of a medicament distally of the balloon.

In other procedures, a balloon-bearing catheter typically with somewhat smaller diameter than a catheter used in PTA or PCTA might be used. Generally, the procedure might be considered to be similar to those procedures in that a comparatively larger more guiding catheter is initially placed so that its distal end is near the site to be treated or diagnosed. A balloon catheter, perhaps with a guidewire extending through an existing central lumen, is then extended from the distal end of the guiding catheter to the desired treatment site. The balloon is then expanded and once the procedure is complete, the balloon deflated and removed from the body. Often, the balloon is of a more compliant nature than of the fixed diameter configuration found in a typical PCTA balloon.

The advent of interventional radiology as a viable alternative in the neurological regions of the body has produced demands on catheterization equipment not faced by demands placed on PCTA devices. The need for significantly smaller diameter devices and devices which have a variable flexibility and yet are able to resist kinking is significant. Further, because the advent of superior catheters for use in interventional radiology, adjunct equipment for treating those very small regions of the vasculature are also in demand.

A dual balloon catheter assembly having an integrated guidewire is shown in U.S. Pat. No. 5,320,604, to Walker, et al. In that device, the balloons are separated by a waist portion including an infusion section. The infusion section has a number of perforations allowing the waist portion to communicate with the single lumen of a catheter shaft. No distal infusion section is found in the device.

A somewhat basic angioplasty catheter assembly is shown in U.S. Pat. No. 4,646,742, to Packard, et al. The catheter found in Packard et al., in general, is shown to have inner lumen but also an inner tube which may be removed completely for enhanced perfusion or for a replacement with a guidewire. The catheter appears to have but a single distal port, in line with the lumen, from which to perfuse fluids.

A multiple lumen angioplasty balloon catheter having a balloon carried on the distal end of the catheter shaft is shown in U.S. Pat. No. 5,380,282, to Burns. The catheter shown therein includes a distal, radially expandable valve used to limit or block fluid flow between the lumen of the catheter and the patient's body during inflation and deflation of the balloon.

U.S. Pat. No. 5,318,535, to Miraki, describes a low profile, exchangeable, dual lumen perfusion balloon catheter assembly for use in dilatation angioplasty procedures. The outer balloon-bearing member includes infusion ports which are distal of the balloon. That component, however, does not contain any valving apparatus nor does its inner lumen appear to have any communication with the inflatable balloon. The balloon is, instead, inflated using a separate lumen. These ports are used in conjunction with ports more proximally placed to allow passage of blood past a region which is to be treated using the angioplasty balloon.

Target Therapeutics of Fremont, Calif. is the owner by assignment of a number of patents dealing with single lumen low-profile valved balloon catheters. For instance, U.S. Pat. Nos. 5,171,221 and 5,304,198 both to Samson, describe balloon catheters in which a single lumen with a distally placed valve member is used to inflate and deflate the balloon. U.S. Pat. No. 5,437,632, to Engelson, shows a balloon catheter having a number of more proximal segments of varying flexibility.

Other disclosures of distal valve mechanisms used to inflate or deflate a balloon may be found in U.S. Pat. No. 4,848,344 to Sos, et al. (and its reissue, Re 34,633). No distal radially placed infusion orifices may be found in that description.

A similar device is shown in U.S. Pat. No. 5,035,705, to Burns. Burns describes a distal, liquid-tight seal which engages a guidewire. The cooperation between this seal and the guidewire allows inflation and deflation of the balloon.

Another distal valving device is shown in U.S. Pat. No. 5,207,229 to Winters and in 5,454,788 to Walker, et al.

U.S. Pat. No. 4,813,934 to Engleson, et al. and its progeny, U.S. Pat. No. 5,135,494 show another valved balloon catheter having but a single lumen.

A number of catheters which are designed to permit material to exit from the catheter lumen in response to a particular applied pressure are also known. For instance, U.S. Pat. No. 5,250,034 allows such material to exist but has no balloon. Similarly, U.S. Pat. No. 5,267,979 to Appling, permits application of such material. A somewhat similar device is seen in U.S. Pat. No. 5,484,409 except that the device additionally has an expandable balloon which inflates upon application of pressurized fluid as well.

A catheter having no balloon but with a distal atraumatic drug delivery tip potentially with a distally place valve cooperating with a guidewire is found in U.S. Pat. No. 5,380,307, to Chee, et al.

None of the above patents or documents describes a single lumen balloon catheter having a infusion section distal to the catheter and a valve mechanism in the distal end of the catheter assembly.

SUMMARY OF THE INVENTION

This invention is a catheter used for insertion into a lumen within the human body. In general, it is to be used in intravascular lumen but is suitable for treatment of any body lumen or space such as may be found in the genito-urinary systems, the biliary system, or wherever else a remotably controllable balloon is desired.

The physical structure of the inventive balloon catheter includes a distally located infusion section having a distal port open axially to the single lumen of the catheter. The distal infusion section includes a plurality of radial orifices through the catheter wall extending between the inner lumen and the outer surface. These orifices are used to transport fluid within the catheter lumen to the exterior surface. Proximally adjacent the infusion section is the balloon itself. The balloon is configured in such a way that is responsive to pressure of fluid in the inner lumen. That is to say that introduction of fluid into the inner lumen and its retention using valve means will inflate the balloon to a desired size. The balloon may have an inner member such as a braid or coil to provide a measure of patency in the balloon region consistent with the stiffness with the remaining portion of the catheter. The balloon may be either elastomeric or of a fixed size.

The balloon is inflated by use of a cooperatively sized core wire or guidewire. In the variations of the invention described in more detail below, the core wire may utilize a stepped or tapered shape which engages the inner lumen of a distal portion of the infusion section so to close the distal tip opening. Alternatively, the core or guidewire may have a valve member placed upon its shaft and installed on the catheter assembly so that the valve member is either proximal or distal of the catheter distal port. The catheter distal port may have a cooperating valve member placed therein. Finally, the proximal end of the infusion section may have a valve seat in addition to or as an alternative to any valve seat placed distally in the infusion section.

Proximal of the balloon is a simple tubular shaft made up generally of polymer, layers of polymer, or stiffeners such as coils or braided members to provide torqueability and appropriate stiffness. It is also in the scope of this invention to have a variety of regions of differing stiffness in the region proximal of the balloon. Interior to the proximal portion of the catheter assembly and proximal of the balloon is an optional lubricious layer made, perhaps, of a polytetrafluoroethylene (PTFE).

A BRIEF DESCRIPTION OF THE DRAWINGS

DESCRIPTION OF THE INVENTION

Figure 1:
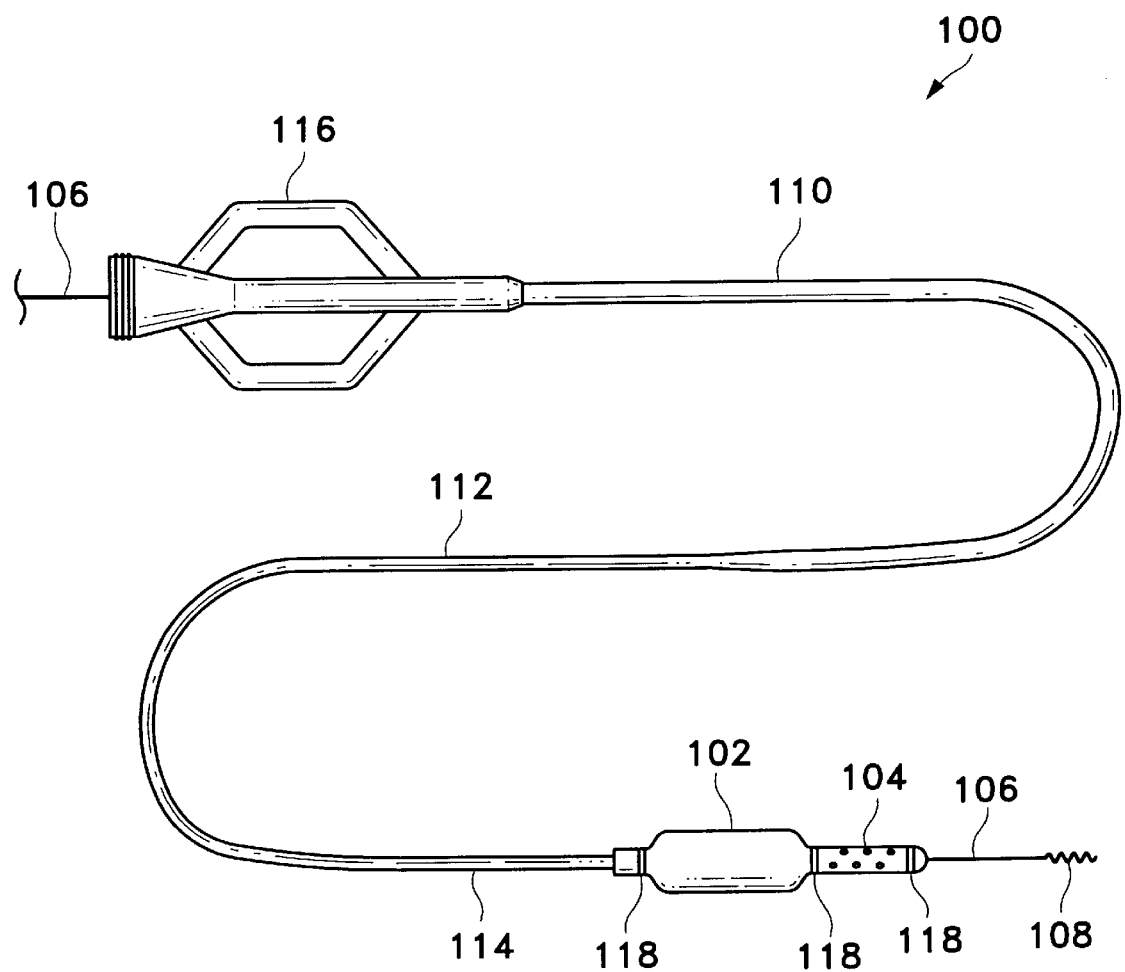
FIG. 1 shows a plan view of the generic variation of the overall assembly of the invention.

FIG. 1 shows a catheter assembly, generally designated (100). The catheter assembly (100) is generally made up of an elongate tubular member having a balloon section (102) just proximally adjacent a infusion section (104). A guidewire (106) having a distal coil (108) typically made of a radio-opaque material such as platinum to provide the guidewire (106) a tip with shapeability and radio-opacity. Proximal of the balloon section (102) is catheter body which in many instances is made up of three, more or less, sections of decreasing stiffness distally. In particular, the most stiff section of catheter (100) is the proximal section (110). In this variation of the invention, the catheter has a section (112) of stiffness intermediate between proximal section (110) and more distal and most flexible section (114). The guidewire (106) may also be seen emanating from the proximal end of the catheter. A fitting (116) having typical threads for attachment to various external equipment is also shown.

Also shown are optional markers (118) which are placed respectively at the distal end of the catheter assembly, at the distal end of the balloon (102), and at the proximal end of the balloon section (102).

This depiction is general in nature and is intended to show only the approximate placement of the elements of this invention. The placement of the apertures shown in infusion section (104) is not important nor is the use of radio-opaque bands (118). One or all of the radio-opaque bands may be omitted and other means chosen for displaying the position of the operative parts of the device within the human body.

The overall length of the catheter assembly (100) is typically between about 30 and 175 centimeters, depending on the portion of the body to reached by catheter (100) through the chosen body access site. For instance, if the chosen site is within the brain and the access site is the femoral artery in the groin region, the length of catheter assembly (100) would be in the higher regions of the noted range. If the access is through the neck, as would be the case with significantly obese patients, the overall length of the catheter can much shorter.

Since one highly desirable use of this catheter assembly (100) is to treat regions of the vasculature within the soft organs of the body such as the liver or brain, it is often desirable to stage the flexibility. That is to say that it is highly desirable that the proximal section of (110) the catheter body be stiffer than the midsection (112) which in turn is stiffer than the more distal section (114) adjacent balloon section (102). At a very general sense, this sequence of flexibilities allows a catheter such as shown here to follow the increasingly more narrow and bending vasculature as the catheter is progressed within the body from the entrance point to the target site within the body. Although the three sections of different flexibility are shown here, again, it is not necessary that the number of sections be only three. It may be four or six or ten, or any other number including a single flexibility, depending upon the needs of the designer providing for the detail variation of this catheter and the needs of the attending physician in introducing it to the chosen site within the human body. Indeed, it may be that one or more or all of the sections may be continuously variable in flexibility as a function of the axial links. For instance, it might be highly desirable to have a proximal section (110) which is of a single flexibility so to allow ease of pushability and access through a guiding catheter and yet have midsection (112) in balloon section (102) be continuously variable in stiffness. That the proximal section (110) is significantly stiffer than the infusion section (104) is the only variation which is significant to this invention.

FIGS. 2A–2G schematically depict a number of variations of the inventive balloon catheter and show the various positions of valve seats in the distal infusion section and the cooperating valve plugs on the core wire or guidewire.

Figure 2A:
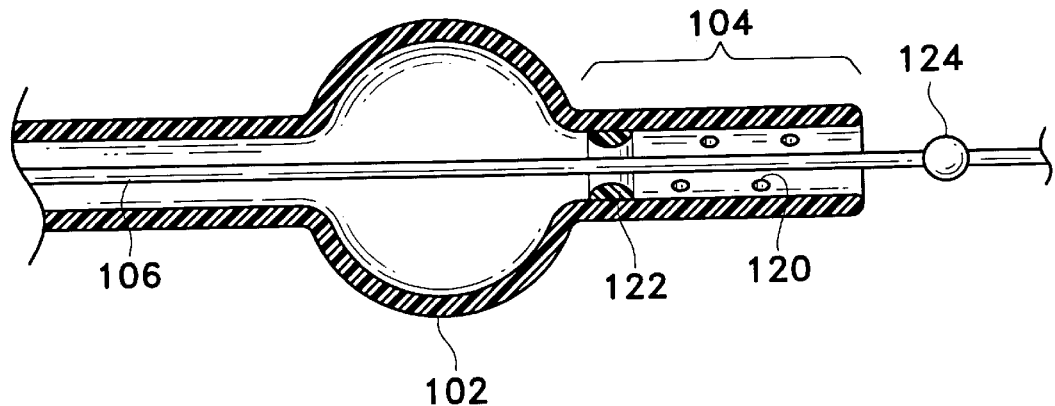
FIGS. 2A–2I show, in schematic cross-sectional fashion, several variations of the invention and depict alternative placements of the valve seats. A valve member on a cooperatively engaging core wire or guidewire.

In FIG. 2A, the infusion section (104) has several orifices (120) passing from the inner lumen to the exterior of the infusion section (104). More specifically, the infusion section contains a valve seat (122) placed proximally in the infusion section (104). The core wire (106) incorporates a valve plug (124) which is, in relation to the valve seat (122), distal to that valve seat (122). In this way, the core wire (106) may be used as a guidewire if so desired. The valve plug (124) is of a size which cooperates the valve seat (122) to close the lumen to flow a fluid either distally from the end of the infusion section (104) or radially through the infusion ports or orifices (120). Addition of fluid to the catheter assembly proximally of the thus-closed valve seat will tend to inflate the balloon (102). The balloon (102) may be either elastic or of a fixed size and, hence, not elastic.

Figure 2B:
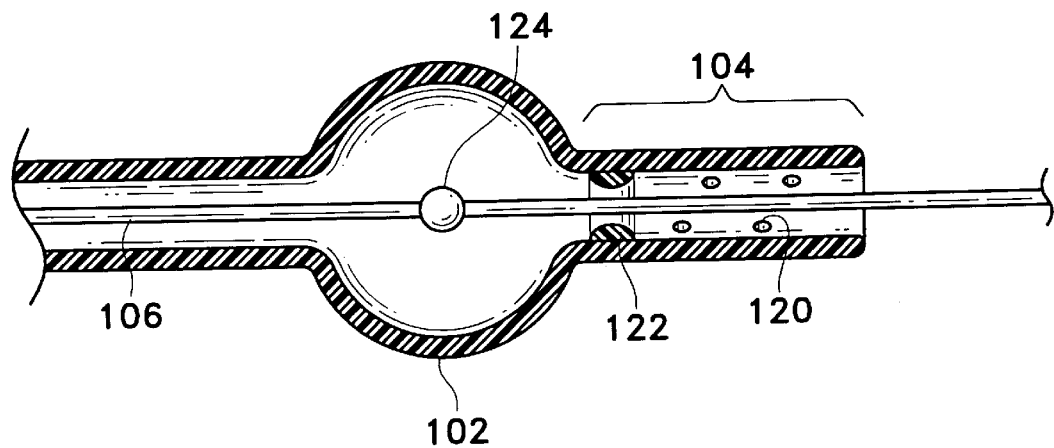

FIG. 2B shows a variation having the identical structure of the infusion section (104) to that shown in FIG. 2A. Specifically, a valve seat (122) is proximally located in the infusion section (104). The core wire (106), however, is situated so that the valve plug (124) fixedly attached to the core wire, is proximally of the valve seat (122). Obviously, this variation may limit the facility of the core wire (106) to be used as a guidewire. Axial distal movement of the core wire (106) will cause the valve plug 124 to engage and seal the valve seat (122). The provision of additional fluid to the catheter lumen will then cause the balloon (102) to inflate.

A conventional guidewire may be used to place the inventive catheter in most of the variations shown herein prior to using the core wire.

The variation shown in FIGS. 2A and 2B allow the use of fairly high fluid pressures to inflate the balloon and yet still permit the use of low infusion pressures prior to the time the valve seat (122) and valve member or plug (124) are engaged.

Figure 2C:
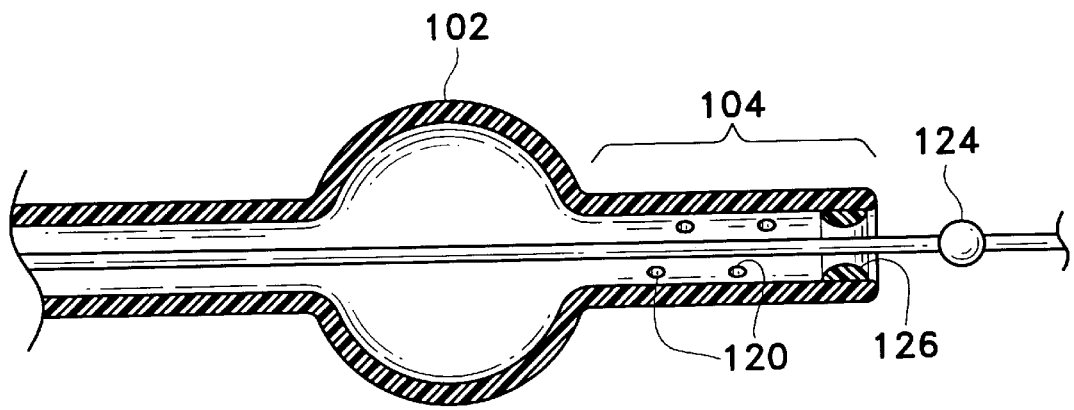
Figure 2D:
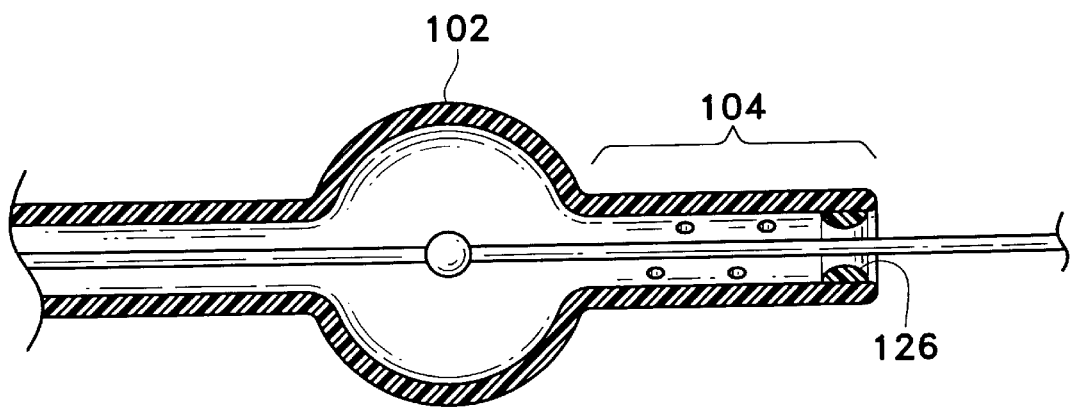

The FIGS. 2C and 2D variations are instead generally useful only in low pressure perfusion and inflation situations.

The FIG. 2C catheters involve an infusion section (104) having a distal valve seat (126). Generally, the valve seat (126) will reside at the distal-most end of the infusion section (104). However, it may be somewhat more proximally, but in this variation, at least one radial infusion orifice (120) must remain proximal of the valve seat (126). The core wire (106) in this variation has a valve member or plug (124) which is distal of the valve seat (126). As was the case with the variation in FIG. 2A, this core wire may be used as a guidewire if otherwise configured to do so. Proximal axial movement of the core wire (106) will cause the valve seat (126) to seat against valve member (104) on the core wire (106) and will both cause the balloon (102) to inflate and the fluid to pass through orifices (120).

The FIGS. 2C and 2D designs may be used, for instance, when the treatment of an artery is desired and the lumen diameter is not substantially larger than the unexpanded diameter of the balloon. Easily expandable balloons, preferably elastomeric, are desired in such cases.

Figure 2E:
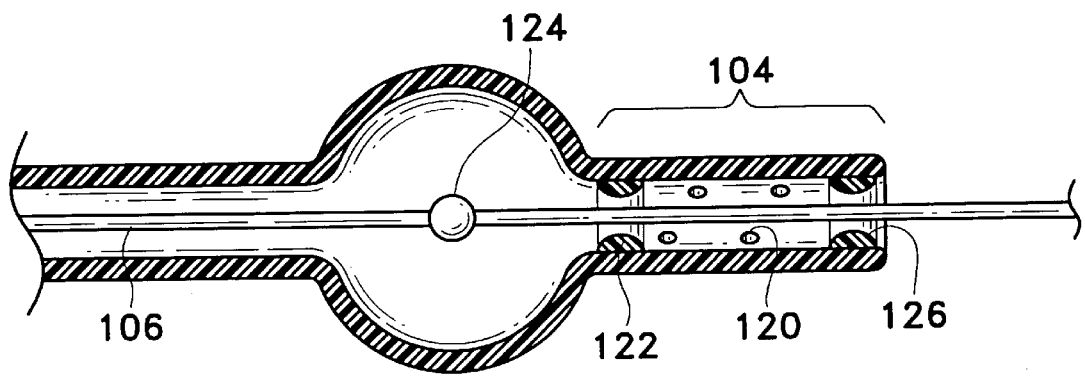
Figure 2F:
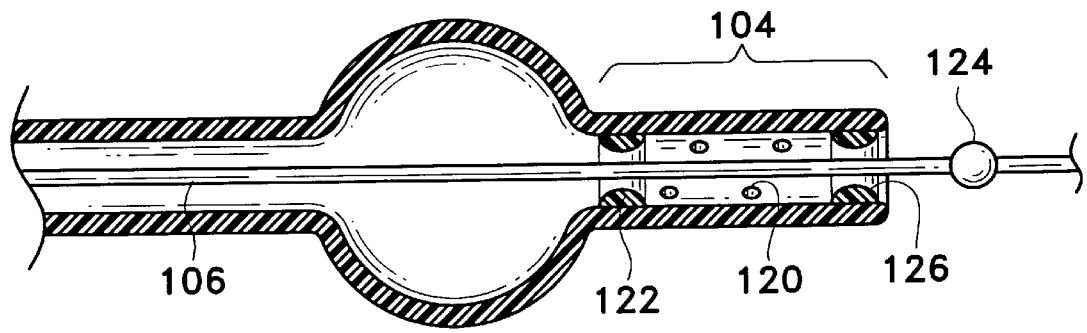
Figure 2G:
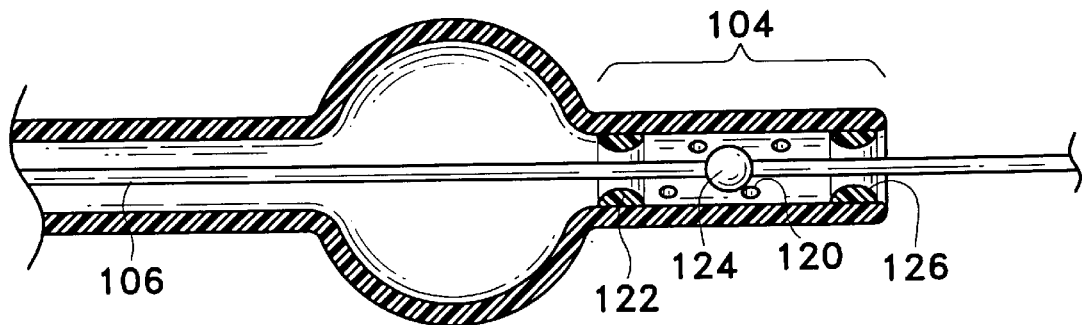

The variations shown in FIGS. 2E, 2F, and 2G utilize an infusion section (104) which has both a proximally located valve seat (122) and a distal valve seat (126). The FIG. 2E variation utilizes a core wire (106) which has the valve member (124) placed proximally of both valve seats (124), (126). The FIG. 2F variation places the valve member (124) distally of both valve seats (124), (126). Finally, the FIG. 2G variation, while more difficult to construct, places the valve member (124) between the two valve seats (124), (126).

The FIGS. 2E and 2F variance may, for instance, be sold as a single kit and used, as chosen, in the same way as the variation shown respectively in FIGS. 2A and 2B. The FIG. 2G variation provides for a variation which is functionally flexible in use. Because the valve member (124) on core wire (106) is placed between the proximal valve seat (122) and the distal valve seat (126), the balloon (102) may be used as a high pressure balloon without concurrent infusion through the infusion ports (150) by axially moving the core wire (106) in a proximal direction to cause the valve member (124) to engage proximal valve seat (122) and to allow the balloon to inflate. Alternatively, the core wire (106) may be moved distally to cause the valve member (124) to engage distal valve seat (126). The latter selection causes any introduction of fluid into the catheter lumen to pass through orifice (120) and (210) to inflate balloon (102) at the same time. Again, the use of the latter selection is typically appropriate in those situations where the balloon is readily inflatable at low fluid pressures and/or the lumen to be treated is not appreciably larger than the diameter of the catheter.

Figure 2H:
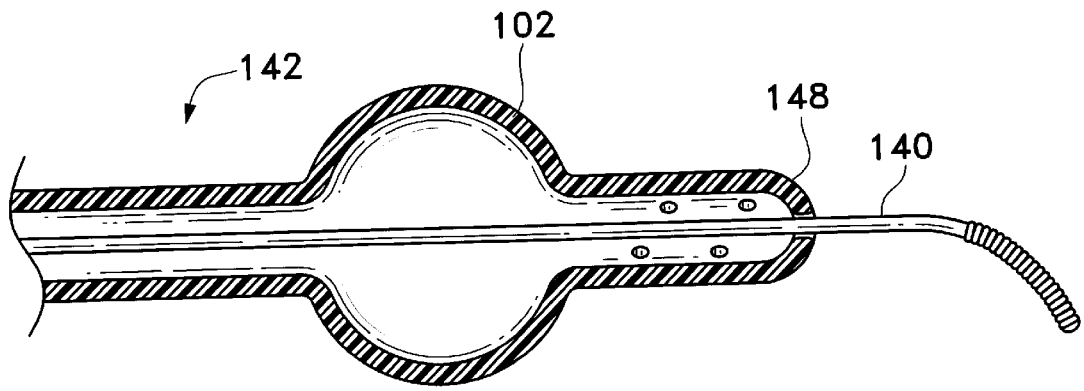
Figure 2I:
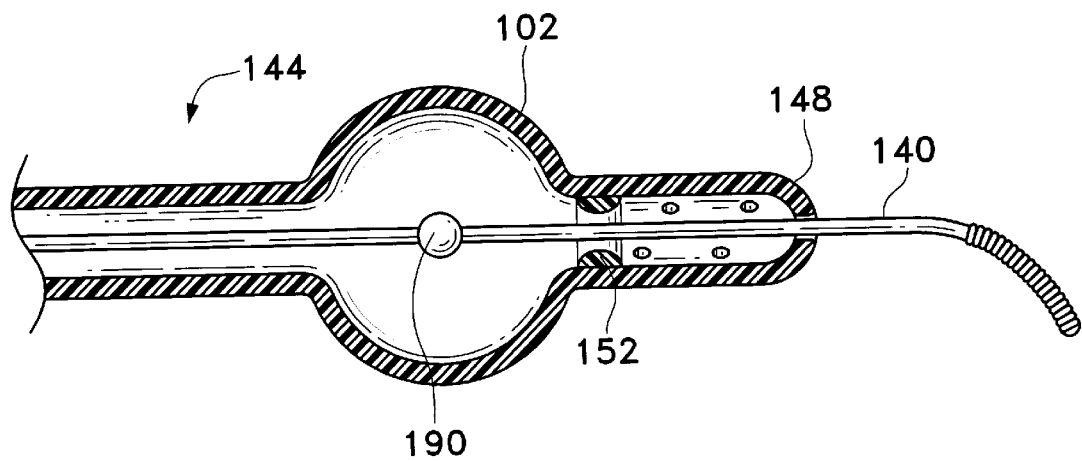

FIGS. 2H and 2I show a further variation of the inventive device in which a core wire (140) having, preferably, a generally constant diameter is useful as a guidewire in guiding the catheter (142, 144) and because of the close fit, e.g., 0.0005 to 0.0015", with the distal tip (148) of the catheter, acts as a metering valve member for the annulus surrounding the core wire (140) at the distal tip (148). That is to say that fluid within the catheter body (142) leaks through the annular space between the core wire (140) and the catheter distal tip at some rate proportional to the pressure of the included fluid no matter what the position of the constant diameter guidewire. A higher pressure imposed upon the interior of the catheter will tend to inflate the balloon (102) as well.

In the FIG. 2I catheter assembly (142), the core wire (140) also has a valve plug (150) and the catheter assembly includes a valve seat (152). The valve plug (150) seats proximally on valve seat (152) to inflate the balloon (102).

Figure 3:
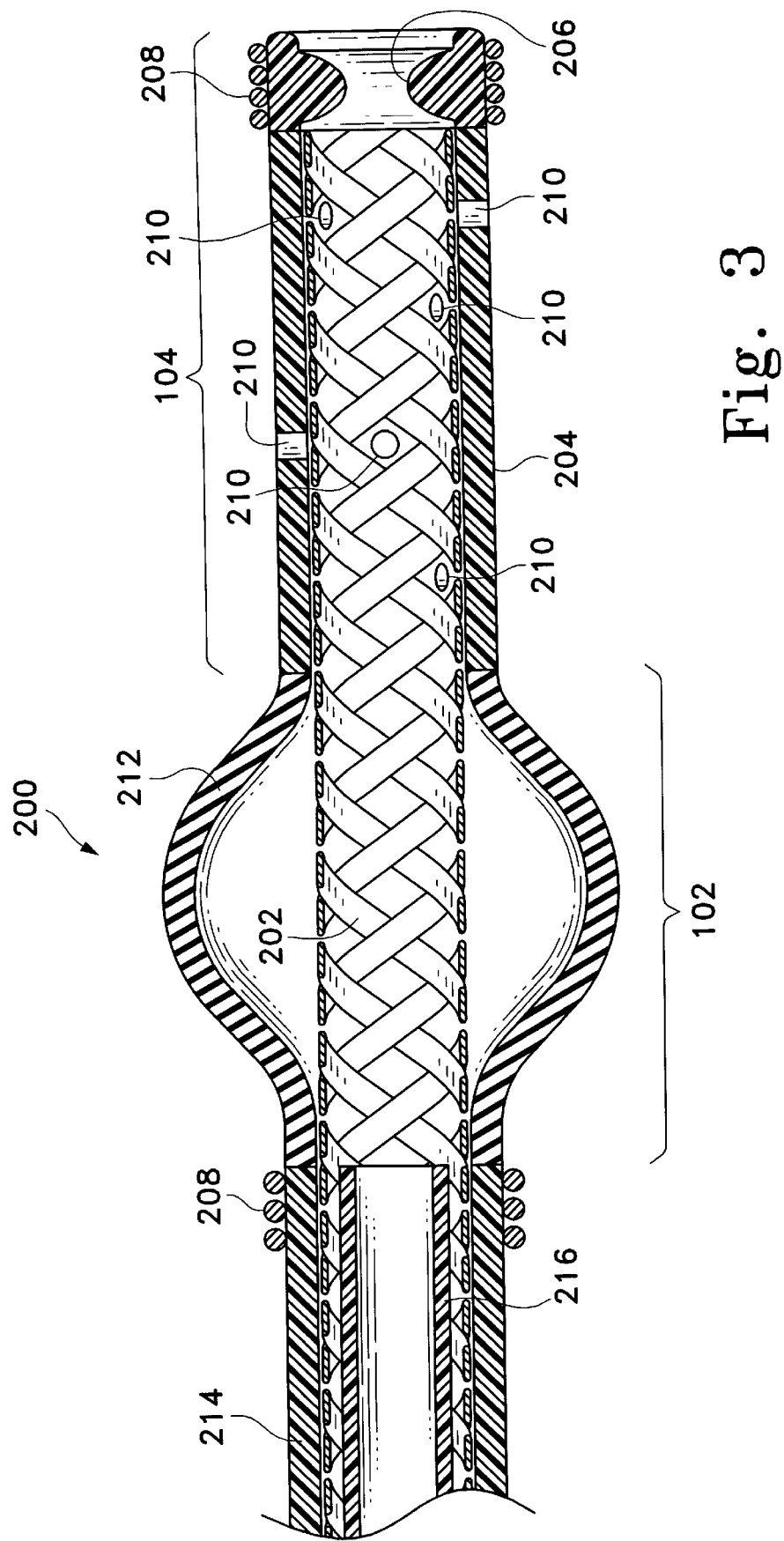
FIG. 3 shows cutaway view of the more distal portion of the inventive catheter having a ribbon braid stiffener in the wall.

As noted above, this invention is a single lumen balloon catheter. FIG. 3 shows a cross-section of one variation of this invention in which a braid (202) is present throughout the majority of the length of the catheter assembly (200) shown in the figure.

The distal infusion section (104) shown in this variation of the invention is made up of an outer polymeric covering (204), of valve member (206) having a smaller inside diameter than the remainder of most of the lumen found in catheter assembly (200), a radio-opaque coil (208) which shows the distal most end of the infusion section (104). Placed throughout infusion section (104) are a number of orifices (210) which pass from the interior of the catheter assembly (200) between the interstices of braid (202) and advance through polymeric outer covering (204) to the outside surface of catheter assembly (200). These passageways fluidly connect the interior of the catheter to its exterior environment. The size of these various orifices (210) and their placement is a matter for the designer of a particular variation of the invention to select. It is possible, for instance, that each of the holes be fairly small so to permit the material introduced into the catheter lumen to be sprayed from the catheter in a number of fine jets. Therefore providing wide dispersal of the introduced material. Such an array of small orifices (110) may also (depending on normal concepts of hydrodynamic flow) produce a high pressure within the catheter so to require the balloon to inflate with speed or with force allowing use of the catheter as one which can compress material found in an artery into the artery wall. Of course, when using this balloon catheter in such a way, it is necessary to use an inelastic balloon material such as is discussed below to allow control of the maximum inflated diameter.

The valve member (206) is intended to be used with a guidewire which passes through the lumen of the catheter assembly and a number of variations of guidewires having valve members which cooperate with valve (see 206) are discussed in the variations found below.

Balloon section (102) is made up of a balloon member (212) and the inner braid (202). The braid (202) is to substantially retain the stiffness of the balloon section (102) in that the elastomeric material used in the balloon (212) is not typically as stiff as the polymer used to make up the body of the catheter proximal of the balloon section (102).

The braid (202) is preferably made up of a number of metallic ribbons, a majority of which comprise materials which are members of a class of alloys known as super-elastic alloys. Preferred super-elastic alloys include the class of titanium/nickel materials known generically as nitinol; alloys which were discovered by the U.S. Naval Ordnance Laboratory. These materials are discussed at length in U.S. Pat. Nos. 3,174,851 to Buehler et al., U.S. Pat. No. 3,351,463 to Rozner et al. and U.S. Pat. No. 3,753,700 to Harrison et al. Commercial alloys containing some amount, commonly up to about 5%, of one or more other members of the iron group, e.g., Fe, Cr, Co, etc., are considered to be encompassed within the class of super-elastic Ni/Ti alloys suitable for this service. When using a braid containing some amount of a super-elastic alloy, an additional step may be desirable to preserve the shape of the stiffening braid. For instance, with a Cr-containing Ni/Ti superelastic alloy which has been rolled into a 1×4 mil ribbon and formed into a 16-member braid, some heat treatment is desirable. The braid may be placed onto a, e.g., metallic mandrel, of an appropriate size and then heated to a temperature of 600° to 750° F. for a few minutes, to set the appropriate shape. After the heat treatment the braid (202) retains its shape and the alloy retains its super-elastic properties.

Other materials which are suitable for the braid (202) include stainless steels (e.g., SS303, SS308, SS310, SS311, ETC.).

Metallic ribbons that are suitable for use in the braid (202) of this invention desirably are between 0.25 mil and 3.5 mil in thickness and 2.5 mil and 12.0 mil in width. The term "ribbon" is meant to include elongated cross-sections such as a rectangle, oval, or semi-oval. When used as ribbons, these cross-sections should have an aspect ratio of thickness-width of at least 0.5.

It is within the scope of this invention that the ribbons or wires making up the braid (202) also contain a minor amount of other materials. Fibrous materials, both synthetic and natural, may also be used. In certain applications, particularly smaller diameter catheter sections, more malleable metals and alloys, e.g., gold, platinum, palladium, rhodium, etc., may be used. A platinum alloy with a few percent of tungsten is sometimes preferred partially because of its radiopacity.

Suitable nonmetallic ribbons or wires include materials such as those made of polyaramides (Kevlar), polyethylene terephthalate (Dacron), polyesters (e.g., Nylon), or carbon fibers. The braids used in this invention may be made using commercial tubular braiders. The term "braid" is meant to include tubular constructions in which the ribbons making up the construction are woven in an in-and-out fashion as they cross, so as to form a tubular member defining a single lumen. The braid members may be woven in such a fashion that 2–4 braid members are woven together in a single weaving path. Typically, this is not the case. It is much more likely that a single-strand weaving path, as is shown in FIG. 3 is used.

The braid shown in FIG. 3 has a nominal pitch angle of 45°. Clearly the invention is not so limited. Other braid angles from 20° to 60° are also suitable. One important variation of this invention is the ability to vary the pitch angle of the braid either as the braid is woven or at the time the braid is included in catheter section or sections. In this way, the braid itself may be used to vary the flexibility of various sections of the catheter.

The balloon (212) itself may be made of a variety of materials depending upon the use to which the catheter is placed. For "non-angioplasty" applications, the balloon is desirably produced from elastomeric material. For angioplasty applications, such may be produced of material such as polyethylene. Polyethylene balloons are not elastomeric.

They are merely folded along their axis to accommodate passage of the distal tip of the catheter assembly through a guiding catheter and then through narrow curvatures. It is difficult to bend such a balloon when it is folded and consequently it is not always as maneuverable as it desirably could be.

An elastomeric balloon, on the other hand, is simply inflatable. It need not be folded. Such elastomeric balloons are suitable for occlusion of vessels for placement of medication or diagnostics and for dilatation of vasospastic vessels, e.g., vessels which open with minimum radial applied force. The catheter design described here is suitable for any size of catheter, but for use in very narrow portions of the vasculature, the axial length of the balloon should be between 2 millimeters and 10 millimeters. The non-expanded diameter may be between 0.035 inches and 0.064 inches for neurosurgical devices. For other uses, the distal end of the catheter (200) may be 0.120 inches. The elastomeric balloon (212) is preferably of a material such as natural or synthetic rubbers, silicones, polyurethanes, and their block or random copolymers. One especially useful class of materials are elastomeric urethane copolymers, e.g., polyurethane/polycarbonate thermoplastics such as Carbothane sold by Thermedics.

Suitable adhesives may be used to seal the balloon (212) against the outer tubing covering (214). A hydrophilic coating over balloons (212) (at least balloons not used for angioplasty) is sometimes desirable.

The balloon section (102) is perhaps the most flexible portion of the catheter assembly and typically comprises about five to 35% of the overall length of the catheter assembly (200).

More proximal of the balloon section (102) is the catheter body. It is made up of an outer layer (214), the braid (202) and an optional inner layer (216). The outer covering (214) and the inner liner (216) are desirably both polymeric. They are desirably selected materials which tack to each other upon heating. They may also be melt miscible. In some instances they may contain components which act in the manner of adhesives, but such is not necessary. Typically, for the variations shown in FIG. 3 the outer covering (214) is of a material is either heat shrinkable onto the inner member (216) and the braid member (202) or may be melted onto those inner members. Preferred materials for the outer layer (214) include such materials as polyethylene, polyvinylchloride (PVC), ethylvinylacetate (EVA), polyethyleneterephthalate (PET), polyamides (such as the Nylons), and polyurethane, and their mixtures and block or random copolymers. PVC and polyurethane are not of the type of polymers which are heat shrinkable onto the outer layer (214) of the polymer section. Other members may be chosen to place these materials on the outer section of the catheter section (200). One such procedure involves slipping the inner section (216) and braid (202) onto a mandrel of appropriate size to support the diameter of the inner section. A length of tubing of a material suitable for the outer covering (214) of a heat-shrinkable tubing exterior is then slipped over the combination of the inner section (216), braid (202) and mandrel. Upon selection of the proper temperature-dependent physical parameters of the respective polymers, the heat-shrink tubing shrinks to squeeze the polymeric material, (e.g. polyurethane) onto the braid when the heat-shrink temperature is above the glass transition temperature of the outer layer polymer (214). The heat-shrinkable tubing may be stripped off before further assembly of the catheter or before use or before certain instances the outer heat-shrink tubing may be allowed to remain in place.

Another useful class of polymers are thermoplastic elastomers, including those containing polyesters as components. Typical of this class of materials is one sold as HYTREL. An adhesive may be coated onto the inner lining of outer tubing member (214) if so desired.

Inner liner (216) is a thin (preferably less than about 0.0015 inches in thickness) tubing of a lubricious polymer such as a polyfluorocarbon. Although a wide variety of materials are generally suitable in this service, thin layers may be made of polytetrafluoroethylene (PTFE) or fluoroethylene polymers (FEP). This inner liner (216) may run from the proximal portion of the catheter assembly (100 in FIG. 1) to the point shown in FIG. 3. It will noted below that the inner tubing member (216) may extend all the way to the distal portion of the catheter assembly (200) if so desired. The fluoropolymers may be etched to provide a surface to which other polymers may adhere. Outer covering (214) may be heated or treated in such a way so to allow penetration of the polymer through the openings in the braid and cause such adherence.

It should be noted that each of the polymers described herein may be doped or filled with radio-opaque materials such as barium sulfate, bismuth trioxide, bismuth carbonate, powdered tungsten, powdered tantalum or the like so that location of various portions of the catheter may be visualized using a fluoroscope.

Figure 4:
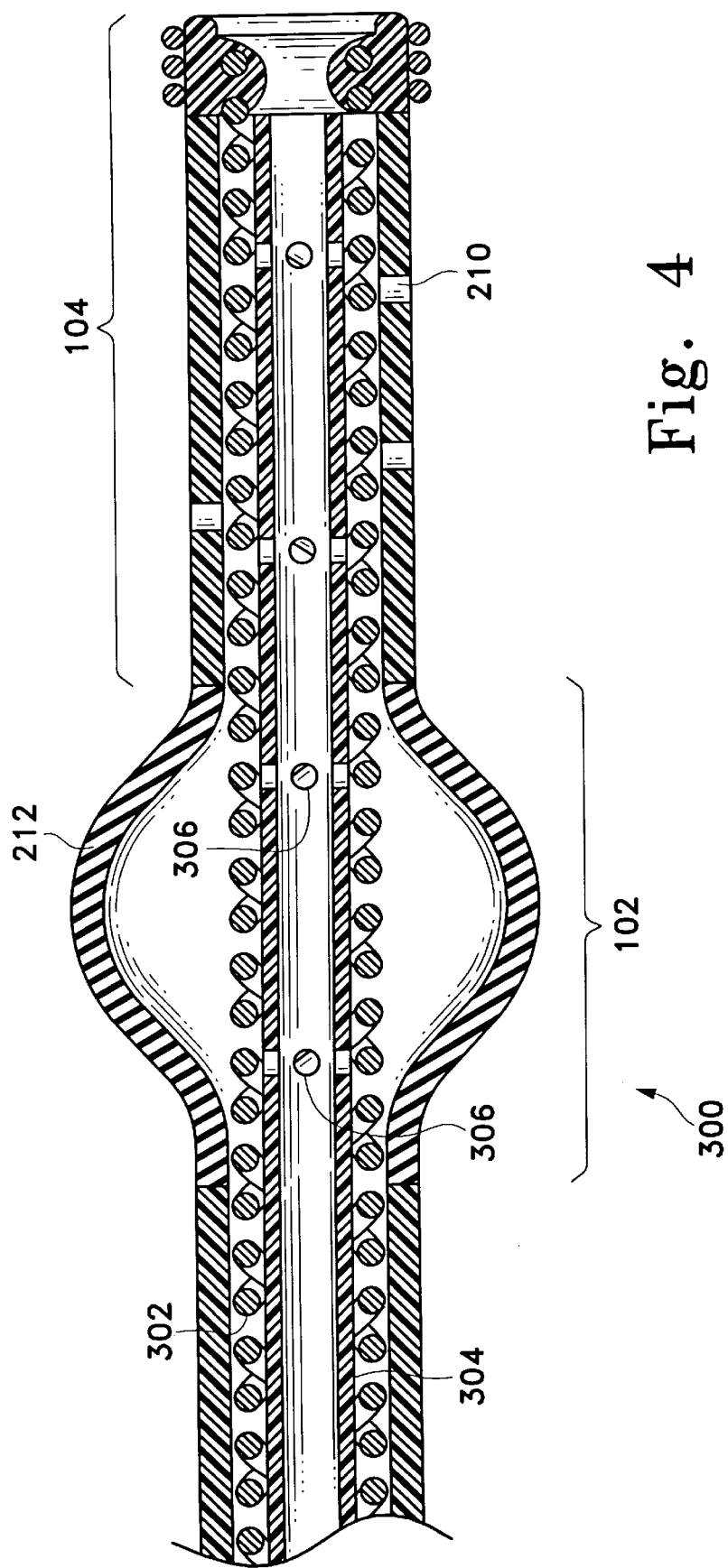
FIG. 4 shows cutaway view of the more distal portion of the inventive catheter having a wire braid stiffener in the wall.

FIG. 4 shows another variation of the invention similarly having a distal infusion section (104) and a balloon section just proximal (102). In general, the only differences between the FIG. 4 variation and the FIG. 3 variation is the use of a braid (302) produced of a round section component or a wire and the fact that the inner liner (304) extends from some location proximal of the catheter portion shown in FIG. 4 and extends all the way to the distal tip. The inner liner (304) also has a number of orifices (306) placed within it so that fluid may readily communicate with balloon (212) and with orifices (210) in the distal infusion section. The presence of a wire-based braid (302) is independent in concept from the use of a inner liner (304) which extends all the way to the distal tip. One may be used without the other or one may be used in combination with other compatible components found in other variations within the scope of this invention.

Figure 5:
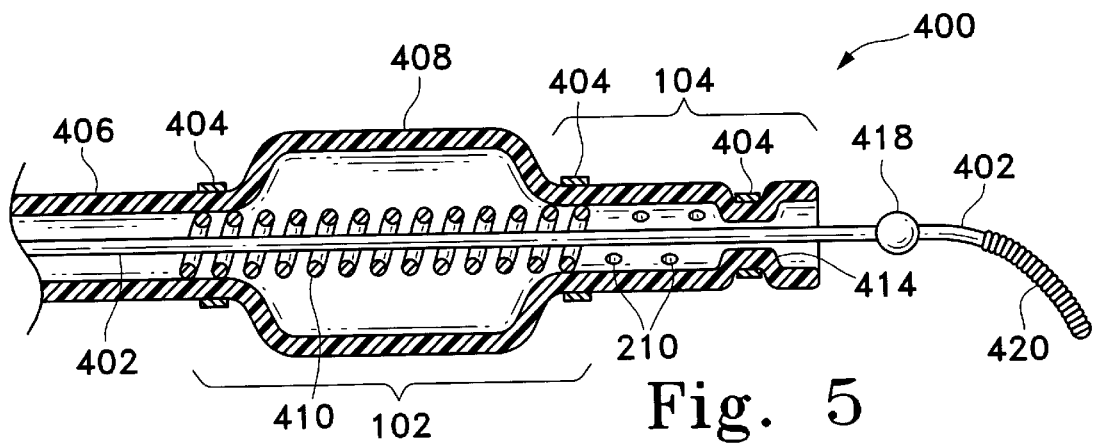
FIG. 5 shows in cross-section, the distal portion of a balloon catheter made according to the invention having a reversible core wire.

FIG. 5 shows still another variation (400) of the invention. In this variation, the core wire (402) is also depicted. In general, it still has the distal infusion section (104) and the just proximal balloon section (102). In this variation, the markers (404) are radio-opaque and, instead of the coils depicted in FIGS. 3 and 4, are radio-opaque bands of metal. The variation in FIG. 5 lacks an inner polymer liner of the type shown in FIGS. 3 and 4. Furthermore, the more proximal section (406) is simply a polymeric tubular member. It may, however, be made of a number of layers of different polymers assembled in known and industry-accepted manner. The balloon (408) shown in this variation is a non-elastic balloon. It has a shape which is more typical to those found in PTA devices as discussed above.

In this variation of the invention, the balloon is stiffened by the use of a coil (410) which expands just the length of the balloon section (102). It is placed there simply to provide a measure of stiffness to that region of the catheter. Additional difference from those variations shown earlier is a use of a valve region (414). The valve region is formed by cinching a portion of the distal infusion section using a radio-opaque band. The valve seat formed in this fashion is typically one which may be used with a core wire (402) and a valve member (418). The device used in the human body may be assembled in such a fashion that the valve member is either distal of valving seat (414) or proximal of valving seat (414) depending, obviously, upon which end of the catheter the wire is placed. Shown at the distal tip of core wire (404) is a coil (420). Coil (420) is typically of a fine, radio-opaque wire material. Platinum with a modest of tungsten is a suitable alloy for such a core wire. The coil allows premanipulation of the tip of the core wire into a shape which allows its use as a guidewire. A guidewire is used to direct, under the assistance of a fluoroscope, the wire through the tortuous vasculature found in the human body. Once the guidewire is moved over a distance, the catheter is slid along the track formed by the guidewire. Once the chosen site is in reach, the guidewire (402) may be retracted to engage valve seat (414). This obviously seals the distal end of catheter assembly (400). A fluid may be then placed through the lumen of the catheter assembly to both inflate balloon (408) and pass through orifices (210) and out into the site to be treated. When the guidewire valve member (418) is introduced into the body such as it is distal of valve seat (414), pushing the guidewire (402) further into the body will release the fluid allowing the balloon (408) to deflate. The catheter may then be withdrawn from the body. Obviously, if the valve member (418) found on core wire (402) is proximal of valve seat (414), the opposite directions are used to inflate and deflate the balloon.

As a matter of completeness, it should be noted that in each variation depicted in the figures, the balloon is shown to be inflated. The deflated balloon in each variation has a much lower profile which approximates the profile of the catheter assembly just adjacent to the balloon itself.

Figure 6:
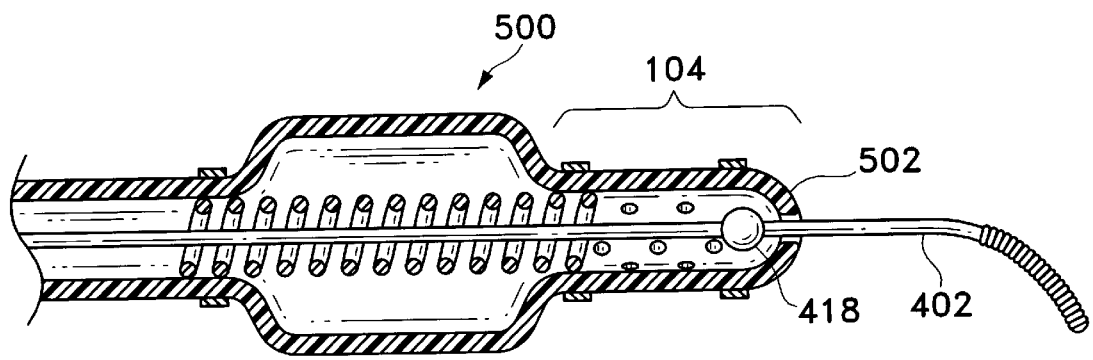
FIG. 6 shows in cross-section, the distal portion of a variation of the inventive catheter having core wire with a valve member actuating from inside the catheter.

FIG. 6 shows still another variation of the invention. In this variation (500), the difference from the FIG. 5 variation is simply that the valving is formed in the infusion section (104) by lowering the overall diameter of the distal tip (502). The core wire (402) and its attendant valve member (418) are in this instance placed proximally of the distal tip (502) of the catheter assembly (500). In this variation of the invention, the valve seat may be assembled (albeit with some difficulty) by insertion of core wire (402) initially through the distal port (502).

Figure 7:
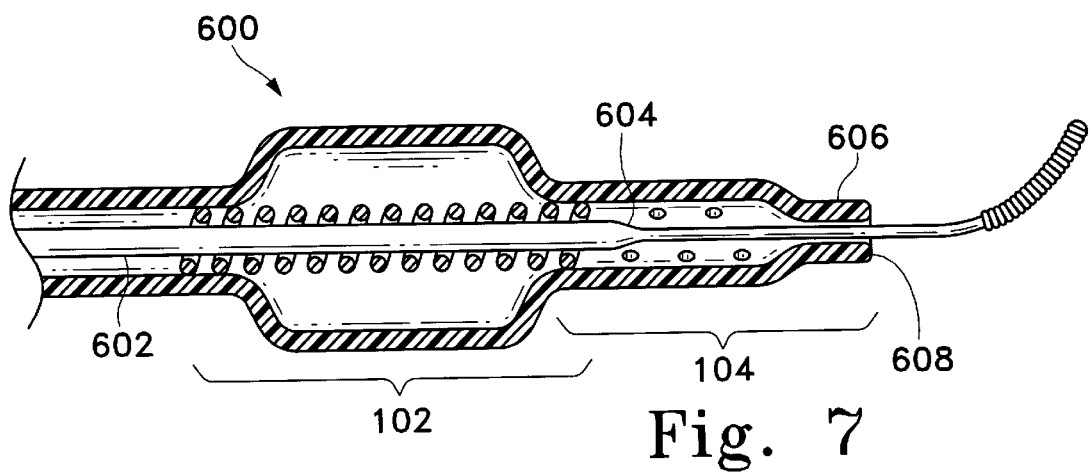
FIG. 7 shows a variation of the inventive catheter in cross-section, showing a tapered core wire as the valving operator.

FIG. 7 shows still another variation (600) of the inventive device. In this variation, the core wire (602) has a sloping shoulder (604) which is adapted to seat with a distal region (606) of infusion section (104). As core wire/guidewire (602) is advanced, the sloping section (604) engages the interior of distal tip (608) sealing that axial hole against further fluid flow.

Figure 8:
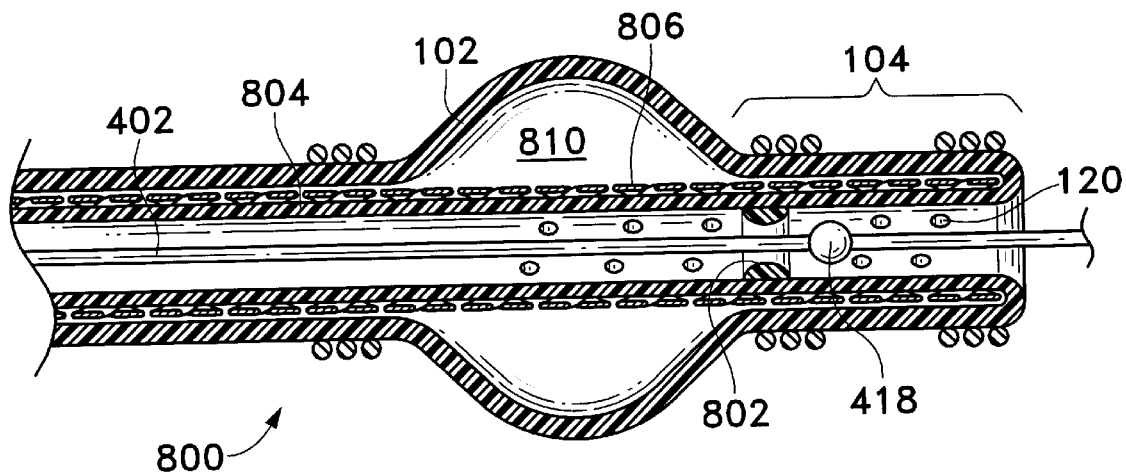
FIG. 8 shows in cross-section, the distal portion of a variation of the inventive catheter in which the valve seat is placed in the proximal end of the infusion section. The core wire is shown with a valve member placed distally of that valve seat.

FIG. 8 shows another variation of this invention. In this variation (800), the catheter infusion section (104) includes a valve seat (802) located proximally in that section. Core wire (402) with its attendant valve member (418) are also shown in FIG. 8. In this instance, valve plug (418) is shown to be distal of valve seat (802). In general, this variation is that shown in FIG. 2A except for the increased level of structural detail. This variation has orifices (120) which extend out through the wall of infuision section (104) to the exterior of the infusion section (104). The inner liner (804) (which may be lubricious) further has holes which pass through the liner through the braid (806) and into the space (810) forming the interior of balloon (102).

Figure 9:
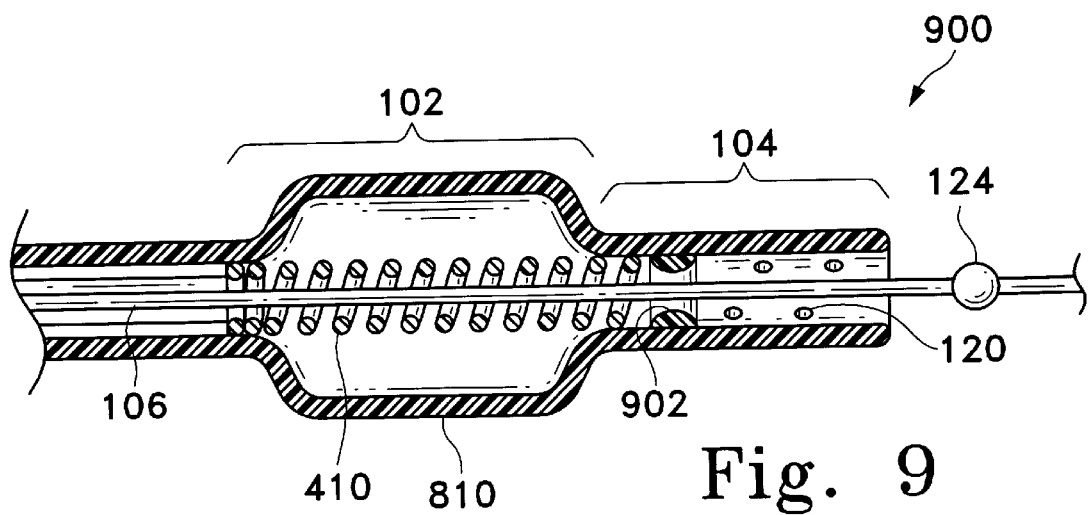
FIG. 9 shows a variation of the device depicted in FIG. 8.

FIG. 9 shows a variation (900) also having a distal section (104) which is used for infusion. In this section (104), the more distal section incorporates a number of orifices (120) which pass through the wall of the catheter to a point exterior of the catheter. The valve seat (902) is placed somewhat proximally in the section (104) but is simply proximal of the infusion orifices (120). It is somewhat midway in infusion section (104), but functionally is in a proximal position. This variation (900) is similar to other variations shown in FIGS. 4, 5, and 6 in that it utilizes a coil (410) in the balloon section (102). In this variation (900), it should be noted that the valve plug (124) is positioned distally of the valve seat (902). The outline of balloon (810) is one that would be made of a material which is substantially inelastic in these services—that is to say that the balloon is made of a material which is not elastomeric but is of a material of such as polyethylene or the like.

Figure 10:
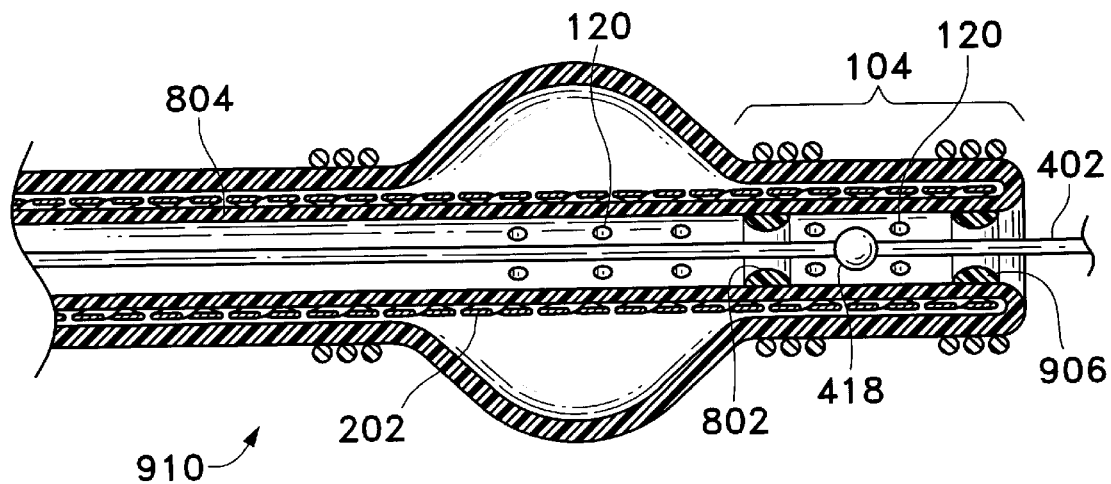
FIG. 10 shows a variation of the inventive balloon catheter in which valve seats are placed at both the distal and the proximal end of the infusion section.

FIG. 10 shows a variation (910) which is very similar in construction to the device shown in FIG. 8. It is different in that the distal infusion section (104) has two valve seats: a proximal seat (802) and a distal valve seat (906) in this. In this variation, the valve member (418) on core wire (402) is placed between the two valve seats (802) and (906). Otherwise the placement of various orifices (120), braid (202), and internal lubricious layer (304) is as shown in FIG. 8. The benefits and operation of this FIG. 10 device are described in the earlier description of FIG. 2G, above.

Each of the features described in this application may be independently combined to utilize their independent contributions to an overall assembly.

Many alterations and modifications may be made by those of ordinary skill in the art without departing from the spirit and scope of this invention. The illustrated embodiments have been shown only for the purposes of clarification. The examples should be not taken as limiting the invention defined in the following claims in any way. Those claims are considered to be of a breadth to include all equivalents, whether those equivalents are now or later devised.

We claim as our invention:

1. A balloon catheter assembly comprising an elongate tubular member having:
   a.) a distal end,
   b.) a proximal end,
   c.) a single, central lumen extending between said distal end and said proximal end and terminating in a terminal axial orifice at said distal end,
   d.) a distally located infusion section having a tubular wall, at least one valving seat located in said infusion section, said valving seat cooperatively engageable with a valve surface on a core wire locatable in said central lumen, and a plurality of orifices extending through said tubular wall,
   e.) a balloon section proximally adjacent said distally located infusion section and in fluid communication with said lumen, and
   f.) a shaft section having a distal end and a proximal end and which shaft section is located proximally in said catheter assembly and comprising a braided member.

2. The balloon catheter assembly of claim 1 wherein the balloon section comprises a balloon of an elastic material.

3. The balloon catheter assembly of claim 1 wherein the balloon section comprises a fixed diameter inflatable balloon.

4. The balloon catheter assembly of claim 1 wherein the shaft section further comprises a lubricious inner liner member defining the central lumen.

5. The balloon catheter assembly of claim 1 wherein the proximal end of the shaft section is stiffer than the distal end of the shaft section.

6. The balloon catheter assembly of claim 5 wherein the shaft section has at least three portions, the most proximal portion being the stiffest, the most distal portion being the least stiff, and said at least one remaining portion having a flexibility intermediate that of the most proximal portion and the most distal portion.

7. The balloon catheter assembly of claim 1, further comprising a core wire extending through the central lumen and having thereon a cooperating valve plug engageable with said at least one valving seat either distally or proximally.

8. The balloon catheter assembly of claim 1, further comprising a core wire extending through the central lumen and having thereon a cooperating tapering surface engageable with said at least one valving seat.

9. The balloon catheter assembly of claim 1, wherein said infusion section contains a distal orifice, and further comprising a core wire extending through the central lumen and wherein the distal orifice in said infusion section forms an annulus having an outer diameter smaller than an inner diameter of said central lumen.

10. The balloon catheter assembly of claim 1 wherein the braided member extends from said shaft section proximal end to a location distal of the balloon section.

11. The balloon catheter assembly of claim 1 wherein the shaft section further comprises an outer covering member exterior to the braided member.

12. The balloon catheter assembly of claim 1 wherein the braided member is a woven braid.

13. The balloon catheter assembly of claim 1 wherein the braided member is an unwoven braid.

14. A balloon catheter assembly comprising an elongate tubular member having:
a.) a distal end,
b.) a proximal end,
c.) a single, central lumen extending between said distal end and said proximal end and terminating in a terminal axial orifice at said distal end,
d.) a distally located infusion section having a tubular wall, at least one valving seat located in said infusion section, said valving seat cooperatively engageable with a valve surface on a core wire locatable in said central lumen, and a plurality of orifices extending through said tubular wall,
e.) a balloon section proximally adjacent said distally located infusion section, and
f.) a braided shaft section comprising a braided member, said shaft section having a distal end and a proximal end and which shaft section is located proximally in said catheter assembly.

15. The balloon catheter assembly of claim 14 wherein the balloon section comprises a balloon of an elastic material.

16. The balloon catheter assembly of claim 14 wherein the balloon section comprises a fixed diameter inflatable balloon.

17. The balloon catheter assembly of claim 14 wherein the shaft section further comprises a lubricious inner liner member defining the central lumen.

18. The balloon catheter assembly of claim 14 wherein the proximal end of the shaft section is stiffer than the distal end of the shaft section.

19. The balloon catheter assembly of claim 18 wherein the shaft section has at least three portions, the most proximal portion being the stiffest, the most distal portion being the least stiff, and said at least one remaining portion having a flexibility intermediate that of the most proximal portion and the most distal portion.

20. The balloon catheter assembly of claim 14 wherein the braided member extends from said shaft section proximal end to a location distal of the balloon section.

21. The balloon catheter assembly of claim 14 wherein the shaft section further comprises an outer covering member exterior to the braided member.

22. The balloon catheter assembly of claim 14 wherein the braided member is a woven braid.

23. The balloon catheter assembly of claim 14 wherein the braided member is an unwoven braid.

24. The balloon catheter assembly of claim 14, further comprising a core wire extending through the central lumen and having thereon a cooperating valve plug engageable with said at least one valving seat either distally or proximally.

25. The balloon catheter assembly of claim 14, further comprising a core wire extending through the central lumen and having thereon a cooperating tapering surface engageable with said at least one valving seat.

26. The balloon catheter assembly of claim 14, wherein said infusion section contains a distal orifice, and further comprising a core wire extending through the central lumen and wherein the distal orifice in said infusion section forms an annulus having an outer diameter smaller than an inner diameter of said central lumen.

27. A balloon catheter assembly comprising an elongate tubular member having:
a.) a distal end,
b.) a proximal end,
c.) a single, central lumen extending between said distal end and said proximal end and terminating in a terminal axial orifice at said distal end,
d.) a distally located infusion section having a tubular wall, at least one valving seat located in said infusion section, and a plurality of orifices extending through said tubular wall,
e.) a balloon section proximally adjacent said distally located infusion section, wherein said valving seat is cooperatively engageable with a valve surface on a core wire locatable in said central lumen to direct fluid from said central lumen into said balloon section to inflate said balloon section, and
f.) a shaft section having a distal end and a proximal end and which shaft section is located proximally in said catheter assembly.

28. The balloon catheter assembly of claim 27 wherein the balloon section comprises a balloon of an elastic material.

29. The balloon catheter assembly of claim 27 wherein the balloon section comprises a fixed diameter inflatable balloon.

30. The balloon catheter assembly of claim 27 wherein the shaft section further comprises a lubricious inner liner member defining the central lumen.

31. The balloon catheter assembly of claim 27 wherein the proximal end of the shaft section is stiffer than the distal end of the shaft section.

32. The balloon catheter assembly of claim 31 wherein the shaft section has at least three portions, the most proximal portion being the stiffest, the most distal portion being the least stiff, and said at least one remaining portion having a flexibility intermediate that of the most proximal portion and the most distal portion.

33. The balloon catheter assembly of claim 27, further comprising a core wire extending through the central lumen and having thereon a cooperating valve plug engageable with said at least one valving seat either distally or proximally.

34. The balloon catheter assembly of claim 27, further comprising a core wire extending through the central lumen and having thereon a cooperating tapering surface engageable with said at least one valving seat.

35. The balloon catheter assembly of claim 27, wherein said infusion section contains a distal orifice, and further comprising a core wire extending through the central lumen and wherein the distal orifice in said infusion section forms an annulus having an outer diameter smaller than an inner diameter of said central lumen.

36. The balloon catheter assembly of claim 27 wherein the braided member extending from said shaft section proximal end to a location distal of the balloon section.

37. The balloon catheter assembly of claim 27 wherein the shaft section further comprises an outer covering member exterior to the braided member.

38. The balloon catheter assembly of claim 27 wherein the braided member comprises a woven braided member.

39. The balloon catheter assembly of claim 27 wherein the braided member comprises an unwoven braided member.

* * * * *